United States Patent
Pfouts et al.

(10) Patent No.: US 8,689,439 B2
(45) Date of Patent: Apr. 8, 2014

(54) METHOD FOR FORMING A TUBE FOR USE WITH A PUMP DELIVERY SYSTEM

(75) Inventors: Mark D. Pfouts, Galena, OH (US); Philip Anthony O'Donnell, Sligo (IE)

(73) Assignee: Abbott Laboratories, Abbott Park, IL (US)

(*) Notice: Subject to any disclaimer, the term of this patent is extended or adjusted under 35 U.S.C. 154(b) by 539 days.

(21) Appl. No.: 12/896,341

(22) Filed: Oct. 1, 2010

(65) Prior Publication Data

US 2012/0034117 A1 Feb. 9, 2012

(51) Int. Cl.
F04B 43/12 (2006.01)

(52) U.S. Cl.
USPC ..... 29/888.022; 29/428; 29/888; 29/888.452; 414/374; 414/476

(58) Field of Classification Search
USPC ............ 29/402.19, 426.6, 428, 888, 888.022, 29/888.452, 890.053; 414/374, 476, 414/477.7, 477.8
See application file for complete search history.

(56) References Cited

U.S. PATENT DOCUMENTS

| | | | |
|---|---|---|---|
| 4,484,864 A * | 11/1984 | Michel | 417/477.8 |
| 4,487,558 A * | 12/1984 | Troutner | 417/477.7 |
| 4,573,884 A * | 3/1986 | Troutner | 417/374 |
| 4,950,136 A * | 8/1990 | Haas et al. | 417/477.7 |
| 5,259,367 A | 11/1993 | Kirby et al. | |
| 5,263,475 A | 11/1993 | Altermatt et al. | |
| 5,290,520 A | 3/1994 | Maystre et al. | |
| 5,322,073 A | 6/1994 | Michels et al. | |
| 5,328,481 A | 7/1994 | Wang | |
| 5,364,342 A | 11/1994 | Beuchat et al. | |
| 5,413,565 A | 5/1995 | Michels et al. | |
| 5,458,470 A | 10/1995 | Mannhart et al. | |
| 5,470,210 A | 11/1995 | Larsen | |
| 5,499,969 A | 3/1996 | Beuchat et al. | |
| 5,542,921 A | 8/1996 | Meyers et al. | |
| 5,553,485 A | 9/1996 | Kaabi et al. | |
| 5,554,140 A | 9/1996 | Michels et al. | |
| 5,588,815 A | 12/1996 | Zaleski, II | |

(Continued)

FOREIGN PATENT DOCUMENTS

| | | |
|---|---|---|
| EP | 0485342 A1 | 5/1992 |
| EP | 0488609 A1 | 6/1992 |

(Continued)

OTHER PUBLICATIONS

International Search Report and Written Opinion for PCT/US2011/052477; Dec. 21, 2011; 15 pages.

(Continued)

Primary Examiner — Minh Trinh
(74) Attorney, Agent, or Firm — Calfee, Halter & Griswold LLP

(57) ABSTRACT

In a method and system for forming tubing to achieve at least one predetermined performance characteristic relating to the flow of a flowable material therethrough, a relationship is determined between at least one material characteristic of the tubing material, at least one operating parameter of the tube forming machine, and the at least one predetermined performance characteristic of the tubing. Based on this relationship, at least one operating parameter for operation of the tube forming machine to achieve the at least one predetermined performance characteristic is determined. The at least one operating parameter is input into the tube forming machine and the machine is operated to achieve the at least one predetermined performance characteristic.

10 Claims, 5 Drawing Sheets

(56) References Cited

U.S. PATENT DOCUMENTS

| | | |
|---|---|---|
| 5,595,175 A | 1/1997 | Malcher et al. |
| 5,611,464 A | 3/1997 | Tsao et al. |
| 5,628,753 A | 5/1997 | Cracauer et al. |
| 5,634,907 A | 6/1997 | Rani et al. |
| 5,662,928 A | 9/1997 | Braun |
| 5,674,194 A | 10/1997 | Jung et al. |
| 5,676,530 A | 10/1997 | Nazarifar |
| 5,747,824 A | 5/1998 | Jung et al. |
| 5,764,539 A | 6/1998 | Rani |
| 5,800,396 A | 9/1998 | Fanney et al. |
| 5,827,984 A | 10/1998 | Sinnreich et al. |
| 5,841,028 A | 11/1998 | Bray et al. |
| 5,868,718 A | 2/1999 | Pepin et al. |
| 5,871,467 A | 2/1999 | Reuning et al. |
| 5,885,243 A | 3/1999 | Capetan et al. |
| 5,899,674 A | 5/1999 | Jung et al. |
| 5,902,285 A | 5/1999 | Kudsk et al. |
| 5,947,976 A | 9/1999 | Van Noy et al. |
| 5,951,510 A | 9/1999 | Barak |
| 5,961,488 A | 10/1999 | Barak |
| 5,989,212 A | 11/1999 | Sussman et al. |
| 5,997,499 A | 12/1999 | Sussman et al. |
| 6,004,284 A | 12/1999 | Sussman et al. |
| 6,032,073 A | 2/2000 | Effenhauser |
| 6,039,714 A | 3/2000 | Cracauer et al. |
| 6,042,564 A | 3/2000 | Barak |
| 6,059,544 A | 5/2000 | Jung et al. |
| 6,068,853 A | 5/2000 | Giannos et al. |
| 6,080,128 A | 6/2000 | Sussman et al. |
| 6,106,249 A | 8/2000 | Barak |
| 6,109,572 A | 8/2000 | Urban et al. |
| 6,110,162 A | 8/2000 | Sussman et al. |
| 6,179,805 B1 | 1/2001 | Sussman et al. |
| 6,179,808 B1 | 1/2001 | Boukhny et al. |
| 6,196,989 B1 | 3/2001 | Padget et al. |
| 6,206,848 B1 | 3/2001 | Sussman et al. |
| 6,241,700 B1 | 6/2001 | Leukanech |
| 6,258,053 B1 | 7/2001 | Mackool |
| 6,261,283 B1 | 7/2001 | Morgan et al. |
| 6,287,274 B1 | 9/2001 | Sussman et al. |
| 6,293,926 B1 | 9/2001 | Sorensen et al. |
| 6,315,755 B1 | 11/2001 | Sussman |
| 6,319,223 B1 | 11/2001 | Wortrich et al. |
| 6,331,171 B1 | 12/2001 | Cohen |
| 6,332,877 B1 | 12/2001 | Michels |
| 6,336,912 B1 | 1/2002 | Bourguignon |
| 6,398,759 B1 | 6/2002 | Sussman et al. |
| 6,416,777 B1 | 7/2002 | Yaacobi |
| 6,428,502 B1 | 8/2002 | Lang |
| 6,471,676 B1 | 10/2002 | DeLegge et al. |
| 6,478,766 B1 | 11/2002 | Chon |
| 6,491,661 B1 | 12/2002 | Boukhny et al. |
| 6,561,999 B1 | 5/2003 | Nazarifar et al. |
| 6,572,349 B2 | 6/2003 | Sorensen et al. |
| 6,575,929 B2 | 6/2003 | Sussman et al. |
| 6,579,270 B2 | 6/2003 | Sussman et al. |
| 6,589,201 B1 | 7/2003 | Sussman et al. |
| 6,589,204 B1 | 7/2003 | Sussman et al. |
| 6,602,193 B2 | 8/2003 | Chon |
| 6,631,650 B1 | 10/2003 | Espinosa |
| 6,632,214 B2 | 10/2003 | Morgan et al. |
| 6,648,847 B2 | 11/2003 | Sussman et al. |
| 6,669,950 B2 | 12/2003 | Yaacobi |
| 6,676,628 B2 | 1/2004 | Sussman et al. |
| 6,740,074 B2 | 5/2004 | Morgan et al. |
| 6,743,245 B2 | 6/2004 | Lobdell |
| 6,770,056 B2 | 8/2004 | Price et al. |
| 6,824,525 B2 | 11/2004 | Nazarifar et al. |
| 6,843,780 B2 | 1/2005 | Larrain et al. |
| 6,860,868 B1 | 3/2005 | Sussman et al. |
| 6,863,073 B2 | 3/2005 | D'Amico et al. |
| 6,868,720 B2 | 3/2005 | Lobdell et al. |
| 6,875,194 B2 | 4/2005 | MacKool |
| 6,908,451 B2 | 6/2005 | Brody et al. |
| 6,921,385 B2 | 7/2005 | Clements et al. |
| 6,955,073 B2 | 10/2005 | Morgan et al. |
| 6,962,488 B2 | 11/2005 | Davis et al. |
| 7,014,629 B2 | 3/2006 | Mackool |
| 7,060,050 B2 | 6/2006 | Kliem et al. |
| 7,070,578 B2 | 7/2006 | Leukanech et al. |
| 7,121,143 B2 | 10/2006 | Malmstrom et al. |
| 7,150,727 B2 | 12/2006 | Cise et al. |
| 7,160,268 B2 | 1/2007 | Darnell et al. |
| 7,169,755 B2 | 1/2007 | Shah et al. |
| 7,172,578 B2 | 2/2007 | Mackool |
| 7,192,419 B2 | 3/2007 | Larrain et al. |
| 7,201,738 B1 | 4/2007 | Bengmark |
| 7,226,435 B2 | 6/2007 | Darnell |
| 7,244,240 B2 | 7/2007 | Nazarifar et al. |
| 7,350,669 B2 | 4/2008 | Rani |
| 7,351,219 B2 | 4/2008 | MacKool |
| 7,392,144 B2 | 6/2008 | Sorensen et al. |
| 7,393,189 B2 | 7/2008 | Davis et al. |
| 7,484,769 B2 | 2/2009 | Domash et al. |
| 7,509,831 B2 | 3/2009 | Khashayar |
| 7,516,741 B2 | 4/2009 | Glusker et al. |
| 7,524,299 B2 | 4/2009 | Hopkins et al. |
| 7,559,914 B2 | 7/2009 | Domash et al. |
| 7,569,149 B2 | 8/2009 | Koch et al. |
| 7,572,242 B2 | 8/2009 | Boukhny |
| 7,594,901 B2 | 9/2009 | Hopkins et al. |
| 7,604,615 B2 | 10/2009 | Gao et al. |
| 7,625,388 B2 | 12/2009 | Boukhny et al. |
| 7,644,603 B2 | 1/2010 | Gordon et al. |
| 7,645,255 B2 | 1/2010 | Gordon et al. |
| 7,651,010 B2 | 1/2010 | Orzech et al. |
| RE41,159 E | 3/2010 | Bourguignon |
| 7,677,467 B2 | 3/2010 | Fink et al. |
| 7,695,447 B2 | 4/2010 | Khashayar et al. |
| 7,704,244 B2 | 4/2010 | Boukhny et al. |
| 7,713,202 B2 | 5/2010 | Boukhny et al. |
| 7,713,228 B2 | 5/2010 | Robin |
| 7,727,193 B2 | 6/2010 | Boukhny et al. |
| 7,740,619 B2 | 6/2010 | Pinedjian et al. |
| 7,748,377 B2 | 7/2010 | Smith et al. |
| 7,758,538 B2 | 7/2010 | Boukhny et al. |
| 7,762,978 B2 | 7/2010 | Mackool |
| 7,775,780 B2 | 8/2010 | Hopkins et al. |
| 7,780,633 B2 | 8/2010 | Domash |
| 7,783,346 B2 | 8/2010 | Smith et al. |
| 7,785,782 B2 | 8/2010 | Chien et al. |
| 7,811,255 B2 | 10/2010 | Boukhny et al. |
| 7,814,905 B2 | 10/2010 | Schuler et al. |
| 7,857,794 B2 | 12/2010 | Dimalanta et al. |
| 2003/0030165 A1* | 2/2003 | Centell et al. ............... 264/40.1 |
| 2003/0132552 A1 | 7/2003 | Gamble et al. |
| 2005/0080507 A1* | 4/2005 | Silberg et al. ............... 700/196 |
| 2006/0018275 A1* | 1/2006 | Zumbrum ................... 417/476 |
| 2006/0058740 A1 | 3/2006 | Cise et al. |
| 2010/0082001 A1 | 4/2010 | Beck et al. |
| 2010/0100060 A1 | 4/2010 | Turner |
| 2010/0140288 A1* | 6/2010 | Jones et al. ..................... 222/1 |
| 2010/0152700 A1 | 6/2010 | Paine |
| 2010/0163021 A1 | 7/2010 | Lai |
| 2010/0174241 A1 | 7/2010 | Ebbett et al. |
| 2010/0202907 A1* | 8/2010 | Klein .......................... 417/476 |
| 2010/0282247 A1 | 11/2010 | Kadrichu et al. |
| 2010/0298812 A1 | 11/2010 | Wolkenstorfer |
| 2011/0022023 A1 | 1/2011 | Weitzel et al. |
| 2011/0180172 A1* | 7/2011 | Gledhill et al. ............... 138/111 |

FOREIGN PATENT DOCUMENTS

| | | |
|---|---|---|
| EP | 0540465 A1 | 5/1993 |
| EP | 0736287 A1 | 10/1996 |
| EP | 0559602 B1 | 4/1997 |
| EP | 0627904 B1 | 11/1997 |
| EP | 0733375 B1 | 9/1998 |
| EP | 0657180 B1 | 11/1999 |
| EP | 0812176 B1 | 12/1999 |
| EP | 0962204 A1 | 12/1999 |
| EP | 0732114 B1 | 8/2000 |
| EP | 1027900 A1 | 8/2000 |
| EP | 0776670 B1 | 9/2001 |

(56) References Cited

FOREIGN PATENT DOCUMENTS

| | | |
|---|---|---|
| EP | 0774266 B1 | 10/2001 |
| EP | 0786260 B1 | 12/2001 |
| EP | 1166818 A1 | 1/2002 |
| EP | 1062958 B1 | 4/2002 |
| EP | 0861654 B1 | 5/2002 |
| EP | 1099854 B1 | 5/2002 |
| EP | 0774267 B1 | 6/2002 |
| EP | 0923394 B1 | 6/2002 |
| EP | 0929331 B1 | 9/2002 |
| EP | 1285642 A1 | 2/2003 |
| EP | 0777111 B1 | 9/2003 |
| EP | 0962203 B1 | 9/2003 |
| EP | 1187643 B1 | 9/2003 |
| EP | 0872252 B1 | 10/2003 |
| EP | 1356833 A1 | 10/2003 |
| EP | 1080739 B1 | 3/2004 |
| EP | 0962205 B1 | 7/2004 |
| EP | 1466646 A1 | 10/2004 |
| EP | 1320393 B1 | 11/2004 |
| EP | 1221919 B1 | 2/2005 |
| EP | 1299149 B1 | 9/2005 |
| EP | 1251894 B1 | 12/2005 |
| EP | 1356835 B1 | 1/2006 |
| EP | 1526824 B1 | 2/2006 |
| EP | 1077736 B1 | 3/2006 |
| EP | 1356834 B1 | 6/2006 |
| EP | 1707166 A1 | 10/2006 |
| EP | 1782781 A1 | 5/2007 |
| EP | 1839690 A1 | 10/2007 |
| EP | 1849488 A1 | 10/2007 |
| EP | 1464347 B1 | 1/2008 |
| EP | 1872810 A1 | 1/2008 |
| EP | 1779878 B1 | 4/2008 |
| EP | 1779879 B1 | 4/2008 |
| EP | 1716828 B1 | 5/2008 |
| EP | 1829568 B1 | 6/2008 |
| EP | 1765190 B1 | 7/2008 |
| EP | 1787606 B1 | 8/2008 |
| EP | 1810702 B1 | 10/2008 |
| EP | 1867349 B1 | 11/2008 |
| EP | 2002812 A1 | 12/2008 |
| EP | 1900347 B1 | 4/2009 |
| EP | 1553902 B1 | 5/2009 |
| EP | 2065020 A1 | 6/2009 |
| EP | 1839689 B1 | 8/2009 |
| EP | 1296732 B1 | 11/2009 |
| EP | 1632210 B1 | 12/2009 |
| EP | 1743670 B1 | 1/2010 |
| EP | 1893251 B1 | 1/2010 |
| EP | 2149359 A1 | 2/2010 |
| EP | 2165725 A1 | 3/2010 |
| EP | 1935440 B1 | 4/2010 |
| EP | 2172235 A1 | 4/2010 |
| EP | 1237608 B2 | 5/2010 |
| EP | 2076232 A1 | 5/2010 |
| EP | 1893250 B1 | 6/2010 |
| EP | 1212111 B1 | 7/2010 |
| EP | 1996249 B1 | 9/2010 |
| EP | 1996269 B1 | 9/2010 |
| EP | 2065001 B1 | 10/2010 |
| EP | 1913926 B1 | 12/2010 |
| EP | 1960041 B1 | 12/2010 |
| EP | 1726323 B1 | 2/2011 |
| WO | 9315777 A2 | 8/1993 |
| WO | 9319791 A1 | 10/1993 |
| WO | 9428309 A1 | 12/1994 |
| WO | 9626701 A1 | 9/1996 |
| WO | 9716169 A1 | 5/1997 |
| WO | 9735886 A1 | 10/1997 |
| WO | 9825557 A1 | 6/1998 |
| WO | 9837856 A1 | 9/1998 |
| WO | 9846293 A1 | 10/1998 |
| WO | 9846294 A1 | 10/1998 |
| WO | 9847551 A1 | 10/1998 |
| WO | 0035461 A1 | 6/2000 |
| WO | 0047250 A1 | 8/2000 |
| WO | 0078372 A1 | 12/2000 |
| WO | 0128474 A1 | 4/2001 |
| WO | 0152921 A2 | 7/2001 |
| WO | 0200291 A1 | 1/2002 |
| WO | 03024519 A1 | 3/2003 |
| WO | 03068197 A1 | 8/2003 |
| WO | 2004012636 A2 | 2/2004 |
| WO | 2004012637 A1 | 2/2004 |
| WO | 2004035111 A2 | 4/2004 |
| WO | 2004035112 A2 | 4/2004 |
| WO | 2004045578 A2 | 6/2004 |
| WO | 2004045705 A1 | 6/2004 |
| WO | 2004055198 A2 | 7/2004 |
| WO | 2004073546 A2 | 9/2004 |
| WO | 2004073751 A2 | 9/2004 |
| WO | 2005092022 A2 | 10/2005 |
| WO | 2005092023 A2 | 10/2005 |
| WO | 2005092047 A2 | 10/2005 |
| WO | 2005104979 A1 | 11/2005 |
| WO | 2006026154 A2 | 3/2006 |
| WO | 2006044029 A2 | 4/2006 |
| WO | 2007001502 A2 | 1/2007 |
| WO | 2007001503 A2 | 1/2007 |
| WO | 2007100741 A2 | 9/2007 |
| WO | 2007109382 A2 | 9/2007 |
| WO | 2007109383 A2 | 9/2007 |
| WO | 2007109413 A2 | 9/2007 |
| WO | 2008011220 A2 | 1/2008 |
| WO | 2008036462 A2 | 3/2008 |
| WO | 2008055876 A1 | 5/2008 |
| WO | 2008046636 A3 | 6/2008 |
| WO | 2008088623 A2 | 7/2008 |
| WO | 2008115270 A2 | 9/2008 |
| WO | 2008117178 A2 | 10/2008 |
| WO | 2008147429 A2 | 12/2008 |
| WO | 2009000786 A2 | 12/2008 |
| WO | 2009089319 A1 | 7/2009 |
| WO | 2009117112 A2 | 9/2009 |
| WO | 2009120184 A2 | 10/2009 |
| WO | 2009140185 A1 | 11/2009 |
| WO | 2009145799 A1 | 12/2009 |
| WO | 2010008424 A2 | 1/2010 |
| WO | 2010030528 A2 | 3/2010 |
| WO | 2010056448 A1 | 5/2010 |
| WO | 2010081838 A2 | 7/2010 |
| WO | 2010088143 A1 | 8/2010 |
| WO | 2010088144 A1 | 8/2010 |
| WO | 2010129128 A1 | 11/2010 |

OTHER PUBLICATIONS

International Preliminary Examination Report for International Application No. PCT/US2011/052477 mailed Jan. 14, 2013.

\* cited by examiner

METHOD FOR FORMING A TUBE FOR USE WITH A PUMP DELIVERY SYSTEM

FIELD

The present disclosure relates generally to the field of extruded tubing for use with medical delivery systems and, more specifically, to methods and systems for extruding such tubing to achieve accurate delivery performance in such systems.

BACKGROUND

Medical delivery pumps are commonly used in delivery systems such as, for example nasogastric, esophagastric, and abdominal feeding systems for feeding flowable, and more typically liquid compositions enterally or intravenously to patients. Many of these pumps include disposable cassettes or peristaltic tubing (otherwise sometimes referred to as a lumen) that inserts into the pump and through which the liquid flows for delivery to the patient.

It is important that such pumps are capable of accurately controlling the flow of liquid to the patient. For peristaltic pumps, in one example, the mechanical dimensions and material properties of the tubing (which is typically a silicone material) are major factors that bear on the delivery accuracy of the pump (e.g., on the accuracy of the volumetric flow). More specifically, tube dimensions such as inner diameter, wall thickness and tube length, and material properties such as the durometer (which generally affects the compressibility of the tube) and Young's modulus (which generally affects the stretchability of the tube), are key properties that affect the delivery accuracy of the pump.

Such tubing is typically extruded, and historically it has been challenging to consistently reduce the delivery accuracy error (e.g., the difference between a predetermined or desired volumetric or dosage delivery through the tube and an actual volumetric or dosage delivery through the tube) to less than about seven percent and more particularly to less than about five percent with an extruded tube. In particular, it is difficult to maintain tight tolerances on the material characteristics of some tubing materials such as silicone. These variations in silicone characteristics (e.g., durometer, elasticity, etc.) cause the delivery accuracy of the pump to vary from one manufacturing lot to another.

A need therefore exists for a tube manufacturing method and system that results in a formed tube sufficient to reduce the delivery accuracy error from one manufacturing lot to another.

SUMMARY

In one aspect, a method for manufacturing tubing to achieve at least one predetermined performance characteristic relating to the flow of a flowable material therethrough generally comprises determining a relationship between the at least one material characteristic of the tubing material, the at least one operating parameter of a tube forming machine, and the at least one predetermined performance characteristic of the tubing. Based on this relationship, at least one operating parameter for operation of the tube forming machine to achieve the at least one predetermined performance characteristic is determined. The at least one operating parameter is input into the tube forming machine, and the tube forming machine is operated to achieve the at least one predetermined performance characteristic.

In another aspect, a set of tubes for discrete, interchangeable use with a pump delivery system to deliver a solution through each of the respective tubes according to a predetermined performance characteristic associated with the pump delivery system generally comprises at least one first tube having a durometer, an elastic modulus, an inner diameter, a wall thickness and a length. The durometer, the elastic modulus, the inner diameter and the length of the at least one first tube together provide a performance characteristic within 7 percent of the predetermined performance characteristic. At least one second tube has a durometer, an elastic modulus, an inner diameter, a wall thickness and a length, with at least one of the durometer and the elastic modulus of the second tube being different from the corresponding one of the durometer and the elastic modulus of the first tube. At least one of the inner diameter, the wall thickness and the length of the second tube is different from the corresponding one of the inner diameter, the wall thickness and the length of the first tube as a function of the difference between the at least one of the durometer and the elastic modulus of the first tube and the corresponding one of the durometer and the elastic modulus of the second tube such that the performance characteristic associated with the second tube is within 7 percent of the predetermined performance characteristic.

In yet another aspect, a system for manufacturing tubing to achieve at least one predetermined performance characteristic relating to the flow of a flowable material therethrough generally comprises a tube forming machine configured to form tubing from a tubing material according to at least one operating parameter of the tube forming machine. A computing device for use with the tube forming machine generally comprises a memory area and a processor coupled to the memory area. The memory area is configured to store data indicative of at least one tubing material characteristic, at least one operating parameter of the tube forming machine, and the effect of the at least one tubing material characteristic and the at least one operating parameter on the at least one predetermined performance characteristic. The processor is programmed to determine, based on at least one material characteristic of a particular tubing material from which tubes are to be formed, at least one operating parameter at which tubes are to be formed from the particular tubing material, the computing device being in communication with the tube forming machine to transmit a signal indicative of the determined at least one operating parameter to the tube forming machine. The tube forming machine is configured to receive the signal from the computing device.

Other features of the invention will be in part apparent and in part pointed out hereinafter.

BRIEF DESCRIPTION OF THE DRAWINGS

Corresponding reference characters indicate corresponding parts throughout the drawings.

DETAILED DESCRIPTION OF THE DRAWINGS

The subject matter described herein is directed to methods and systems for making tubing, and more particularly for extruding tubing and even more particularly for extruding peristaltic tubing for use with peristaltic pump delivery systems. Such tubing according to one embodiment may be used in connection with medical delivery pumps such as pumps used in delivering flowable solutions (e.g., liquids or other flowable solutions) including enterally or intravenously delivered solutions.

Figure 1:
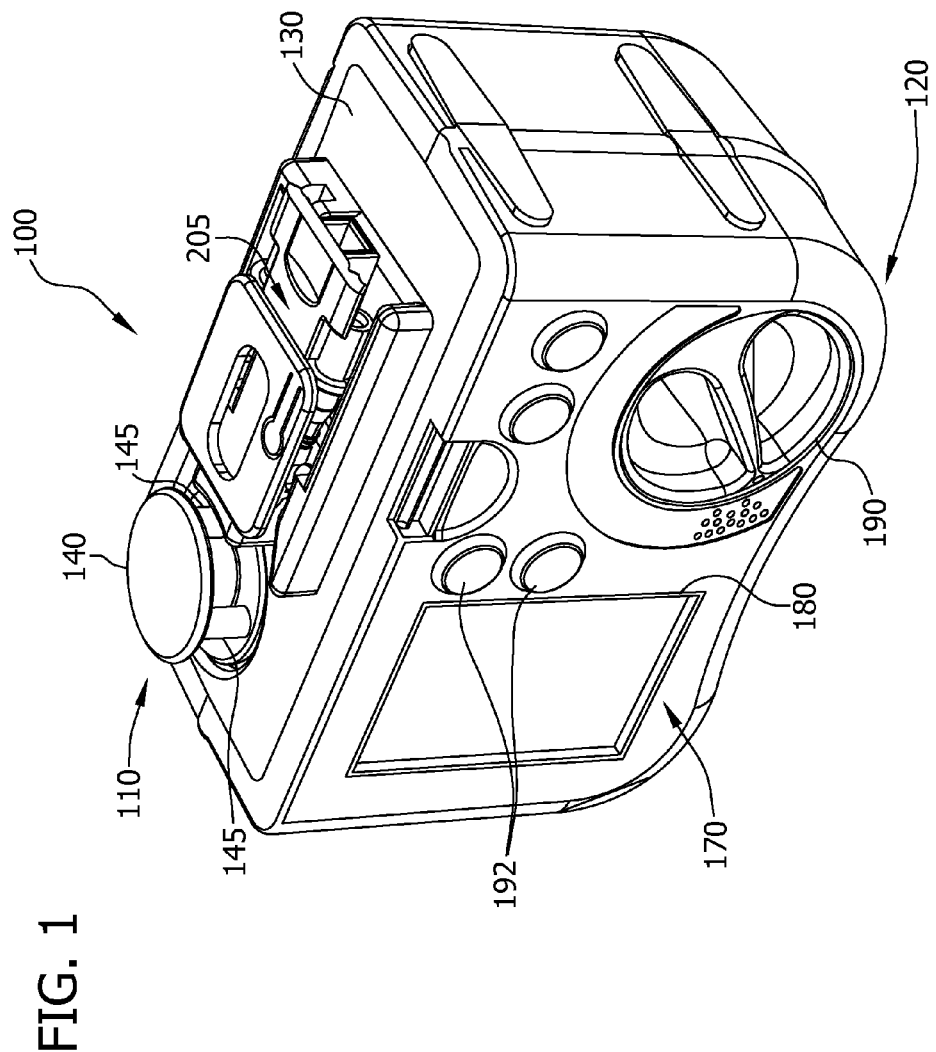
FIG. 1 is an elevated perspective view of one embodiment of an enteral peristaltic pump delivery system incorporating a cassette including peristaltic tubing.

With reference to the drawings and in particular to FIG. 1, in one example tubing made in accordance with the methods and systems disclosed herein may be used in connection with an enteral peristaltic pump delivery system (broadly, a delivery system) 100. The illustrated delivery system 100 includes a peristaltic pump 110 carried by a base 120. A platen 130 is mounted on the base 120 and typically carries a rotor 140 having at least one roller 145.

A pump controller subsystem 170 may also be included that can be remotely operated using Wi-Fi, Bluetooth®, and other types of wireless computer communications capabilities. The illustrated delivery system 100 includes a user display interface 180 that incorporates a touch-sensitive screen to enable user interaction and control of the subsystem 170. Other alternative modifications may include actuators, rotary switches, buttons 192, and switches 190 as depicted in FIG. 1.

The delivery system 100 may be compatible for use with, may include, and/or may cooperate with one or more types of feeding sets such as feeding set 200. The illustrated feeding set 200 is an enteral feeding set that includes, among other components, a cassette (broadly, a carrier) 205, which is depicted in FIG. 1 as being positioned in place and on the platen 130.

Figure 2:
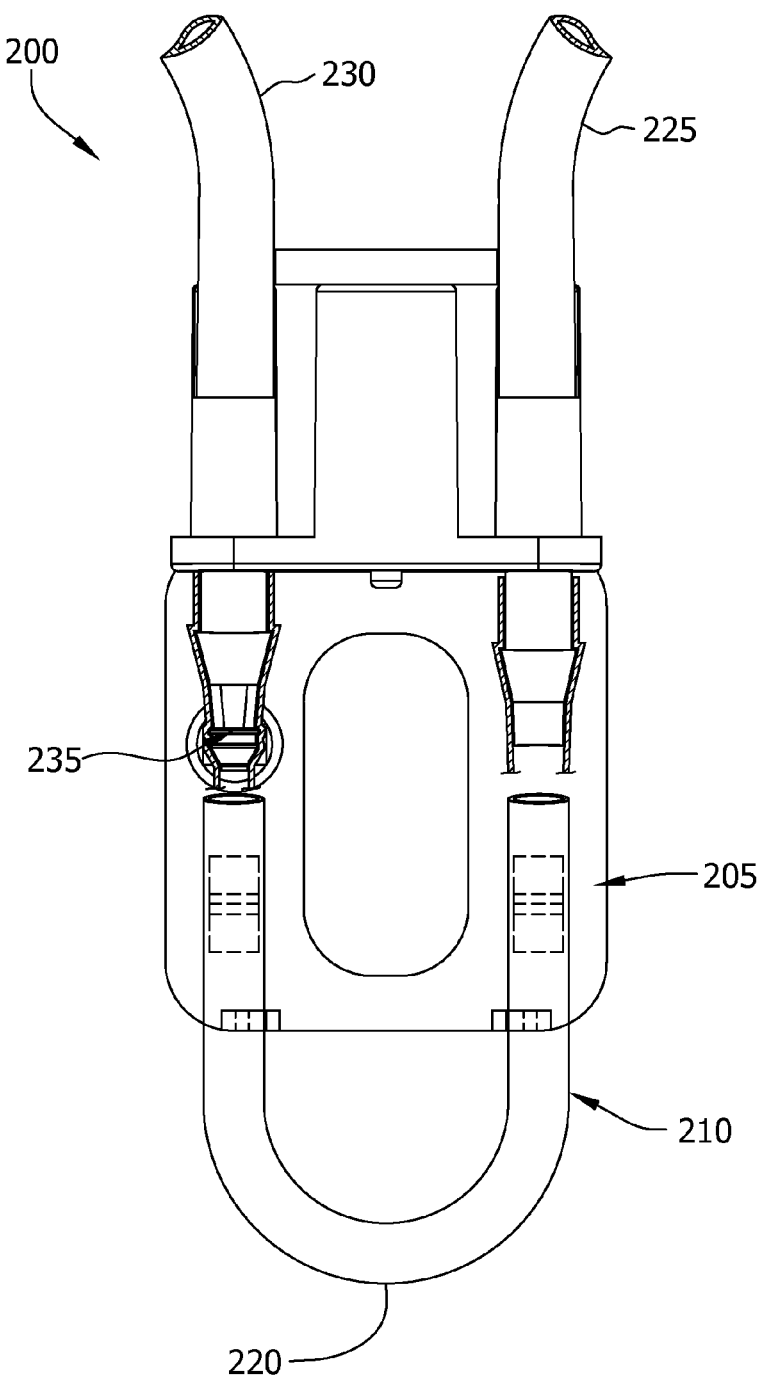
FIG. 2 is a fragmented schematic of the cassette of FIG. 1, including the peristaltic tubing.

As depicted in FIG. 2, the carrier 205 includes and/or carries a substantially flexible lumen (broadly, a tube or tubing) 210, which in the illustrated embodiment includes a substantially extensible or stretchable loop 220. The loop 220 is typically stretched about the rollers 145 of the rotor 140 and positively biased when the carrier 205 is captured on the platen 130.

The tube 210 extends from the carrier 205 to opposite ends that define an inflow end 225 and an outflow end 230. The inflow end 225 of the tube 210 is connected to a suitable source (not shown) of solution to be delivered to a patient, for example, a source of an enteral liquid. The outflow end 230 of the tube 210 is suitably connected to a patient feeding tube (not shown).

The feeding set 200 may include an inline valve 235 that is received within the tube 210. The inline valve 235 is fabricated from a material that has a hardness rating that is more rigid than, harder than, and/or higher than that of the material used to fabricate the tube 210. In other words, the material used to fabricate the tube 210 is more flexible, more stretchable, and/or more ductile than the material selected for the inline valve 235 to create a relative material hardness, rigidity, or deformability differential between the tube 210 and the inline valve 235. In this way, the walls of the tube 210 may be easily stretched, flexed, or deformed without a corresponding and/or comparable deflection, deformation, and/or flexure of the inline valve 235.

During use, the feeding set 200 is primed and the carrier 205 is snapped into place on the platen 130. Thereafter, the pump controller subsystem 170 is actuated to effect feeding of the enteral solution to the patient.

While the methods and systems disclosed herein are particularly useful in connection with extruded tubing for medical delivery systems such as the enteral pump delivery system illustrated in FIG. 1, it is understood that such tubing may be used in any suitable liquid delivery system without departing from the scope of this invention. It is also understood that the tubing may be made other than by extruding and remain within the scope of this invention.

Accordingly, tubing manufactured in accordance with the methods and systems herein will be broadly referred to further as being manufactured by a tube forming machine. The term tube forming machine refers to any machine used to manufacture tubing. In one particularly suitable embodiment the tube forming machined comprises at least an extruder (which allows selection of a predetermined tube inner diameter and/or wall thickness), and in some instances further comprises one or more post-extrusion apparatus for performing further processing of the tube such as cutting the extruded tubing to a predetermined tube length. It is contemplated that the post-extrusion apparatus may be co-located with the extruder (e.g., at a manufacturing site), or such apparatus may be located remote from the extruder, for cutting the tubing to a tube length at a later time.

In accordance with one particularly suitable embodiment, the methods and systems disclosed herein produce tubing that in use achieves at least one predetermined performance characteristic relating to the flow of a flowable material (e.g., a liquid solution or other flowable material to be delivered) therethrough. For example, the at least one predetermined performance characteristic may be a volumetric flow accuracy (broadly, a delivery accuracy) of solution through the tubing. The delivery accuracy as used herein refers to the difference between an actual volumetric or dosage delivery of solution through the tubing and a predetermined nominal or desired volumetric or dosage delivery.

Several factors may affect the delivery accuracy associated with the tubing used in a particular delivery system. For example, tube properties that may affect delivery accuracy include, but are not limited to, at least one dimensional characteristic of the tube including without limitation the inner diameter of the tube, the wall thickness of the tube and the length of the tube. Additional tube properties that bear on delivery accuracy include at least one material property of the material from which the tube is made, including without limitation the durometer of the tube material and the Young's modulus (e.g., the elasticity) thereof.

As one example, the tubing material may include any suitable material such as polymeric materials. More suitably, the tubing material may be, without limitation, silicone and/or other elastomers, a polytetrafluoroethylene (PTFE), a polyvinyl chloride (PVC), and similar materials and combinations thereof. The tubing material used to fabricate the tube 210 will suitably and typically be selected to have a Shore durometer rating of approximately about 10 to about 50 Shore O-scale, and/or about 10 to about 85 Shore A-scale. More suitably, for purposes of operation and in cooperation with pump 110, the tube 210 may have a durometer rating of at least about 30 and more suitably in the range of about 45 to about 85, including in one embodiment from about 45 to about 65 and in another embodiment from about 60 to about 80 on a Shore A-scale. However, it is understood that the flexibility of the tube 210 will depend upon the specific material selected, the viscosity of flowable material to be pumped through the tubing, the geometric and physical configuration of and relationship between the tube 210 and the rollers 145 of the rotor 140, and other considerations and variables.

Even when a particular material is selected for fabricating the tubing, the material properties of the tube material may vary slightly from one material supplier or tube manufacturer to another, or from one material lot to another. For example, one material that is commonly used for making tubes used with peristaltic type pumps, such as the enteral pump of FIG. 1, is silicone. Silicone is typically selected based on nominal (e.g., average, or baseline) material properties. But it is known that actual material properties of silicone such as, without limitation, durometer and elasticity (Young's modulus), will deviate from the nominal material properties from one manufacturing lot to another. These deviations can have a negative effect on the delivery accuracy of tubes made from such materials.

Figure 3:
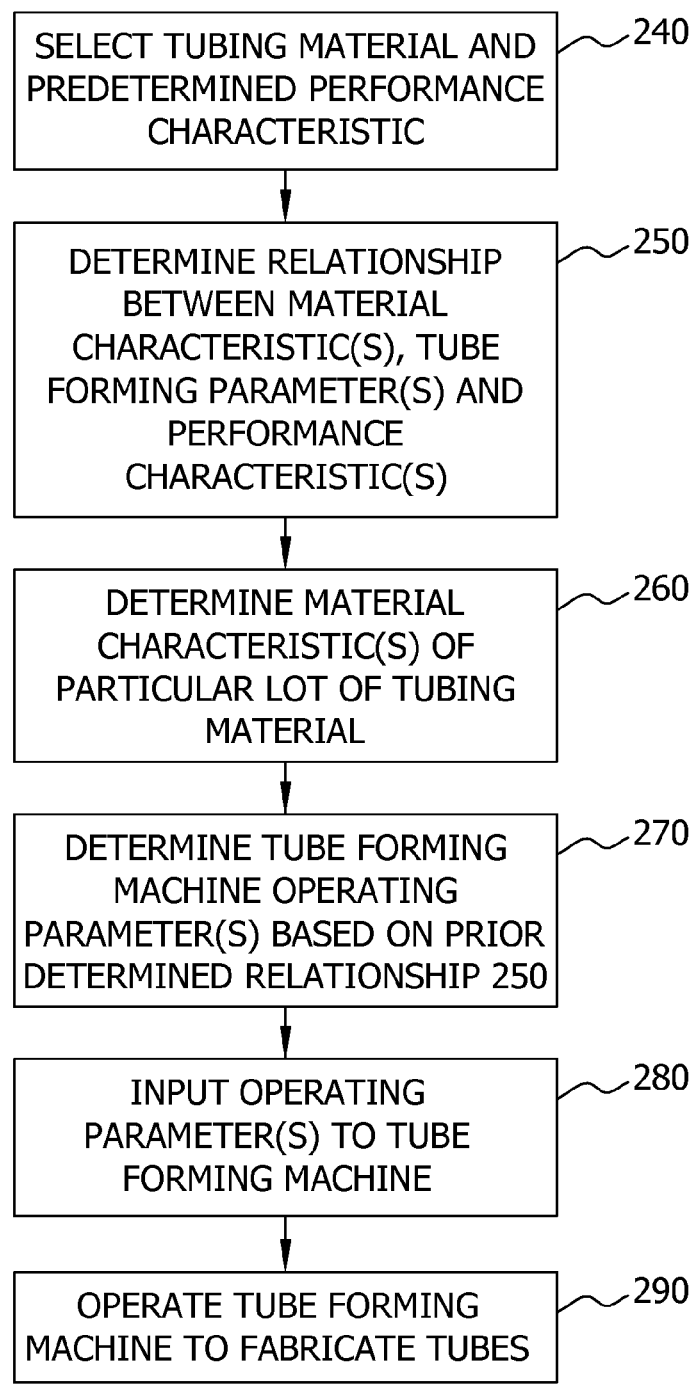
FIG. 3 is a flowchart of one embodiment of a method for manufacturing tubing and in particular peristaltic tubing for use with a delivery system pump such as that of FIG. 1.

With reference to FIG. 3, in accordance with one embodiment of a method for making tubing, and more particularly for extruding tubing, that in use will achieve a predetermined performance characteristic such as delivery accuracy, once a material for making tubing is selected 240 a relationship is first determined 250 between at least one material characteristic of the tubing material and the predetermined performance characteristic. For example, in one embodiment a relationship may be determined between the tubing material durometer and/or the tubing material Young's modulus, and the predetermined (e.g., desired or intended) delivery accuracy provided by the tubing.

In one suitable embodiment, such a relationship may be determined by running multiple experiments using tubes made from materials having different material characteristics (but otherwise the same predetermined or nominal dimensions including inner diameter, wall thickness and length) and measuring the associated delivery accuracy. That is, the operating parameters (configurations and/or control settings) of a tube forming machine (i.e., an extruder and in some instances other post-extrusion apparatus) used to fabricate the tubing include, among other parameters, the inner diameter, wall thickness and length of the tubing.

However, variations in the material characteristics may result in one or more of the actual tube dimensions of tubes fabricated by the tube forming machine at such parameter settings to vary from the intended dimensions. Additionally, or alternatively, variations in the material characteristics of the tubing material may result in different compressibility and/or stretchability of the tubing during use—even if the dimensions of the tubing do not vary from the intended dimensions, and thus bear on delivery accuracy. The results of such experiments are used to develop a functional relationship (e.g., an equation, a look-up table, etc.) between the material properties of the tubing, the operating parameters of the tube forming machine such as for example the inner diameter, wall thickness and/or length of the tubing, and at least one performance characteristic such as the delivery accuracy.

In use further according to the method herein for making and more suitably extruding (and in some instances post extrusion processing) tubing, a tube manufacturer may receive instructions from a customer (either an internal customer or an external customer) to manufacture tubes having predetermined (e.g., intended) dimensions (e.g., inner diameter, wall thickness, and/or length, etc.) and predetermined (e.g., intended or nominal) material properties (e.g., durometer, Young's modulus, etc.). Prior to a particular lot of tubing material being used by the manufacturer for this purpose, the customer and/or the manufacturer determine 260 one or more material characteristics of the tubing material (i.e., one of the material characteristics on which the previously determined functional relationships 250 are based).

In some instances, one or more such material characteristics may be obtained from certification sheets or other information communications from the material supplier identifying such characteristics. Alternatively, or additionally, the customer and/or the manufacturer could test the material for such material characteristics. In this manner, any deviations of the material characteristics from the nominal material characteristics can be identified.

Based on the relationships determined 250 between the at least one material characteristics, operating parameters (e.g., at least one dimensional characteristic such as the inner diameter, wall thickness and/or length) and the at least one predetermined performance characteristic (e.g., delivery accuracy), the actual material characteristics of the material to be used are transformed 270 into at least one operating parameter (e.g., inner diameter, wall thickness, length, etc.) for operation of the tube forming machine (i.e., the extruder and/or other post-extrusion apparatus) in order to produce tubing that will in use achieve the at least one predetermined performance characteristic (e.g., delivery accuracy). For example, in one particularly suitable embodiment dimensional characteristics such as the inner diameter and/or the wall thickness are input to the extruder, whereas a suitable post-extrusion apparatus is used to cut the tubing to a predetermined tube length.

In this manner, deviation(s) of operating parameter(s) of the extruder or other post-extrusion apparatus, and in particular of the resultant dimension(s) of the tubing, account for deviations in the one or more material characteristics of the particular lot of tubing material in order to reduce deviations (e.g., error) in the predetermined performance characteristic such as delivery accuracy.

For example, a customer may determine a theoretical inner diameter, wall thickness and length of a tube to achieve a desired volumetric or dosage delivery through the tube. Based on the determined relationships between the material characteristics, tube dimensions (e.g., as set by the operating parameters of the extruder and/or other post-extrusion apparatus) and delivery accuracy, a manufacturer may determine an actual inner diameter, wall thickness and/or length that is different from the respective theoretical inner diameter, wall thickness and/or length of the tubing to be manufactured in order to compensate for deviations in the material characteristics of different lots of tubing material.

The determined 270 operating parameter, or parameters (e.g., inner diameter and/or wall thickness), are input 280 to the tube forming machine (meaning that the extruder is configured and/or the operating system of the extruder is instructed or set, manually or electronically) and or other post-extrusion apparatus (e.g., a cutting apparatus to cut the tubing to a predetermined tube length) and the extruder/post-extrusion apparatus is/are operated 290 to manufacture tubing that performs at or near (e.g., within about seven percent, more suitably within about five percent and even more suitably within about three percent) the at least one predetermined performance characteristic (e.g., delivery accuracy, and more particularly the volumetric flow rate).

Figure 4:
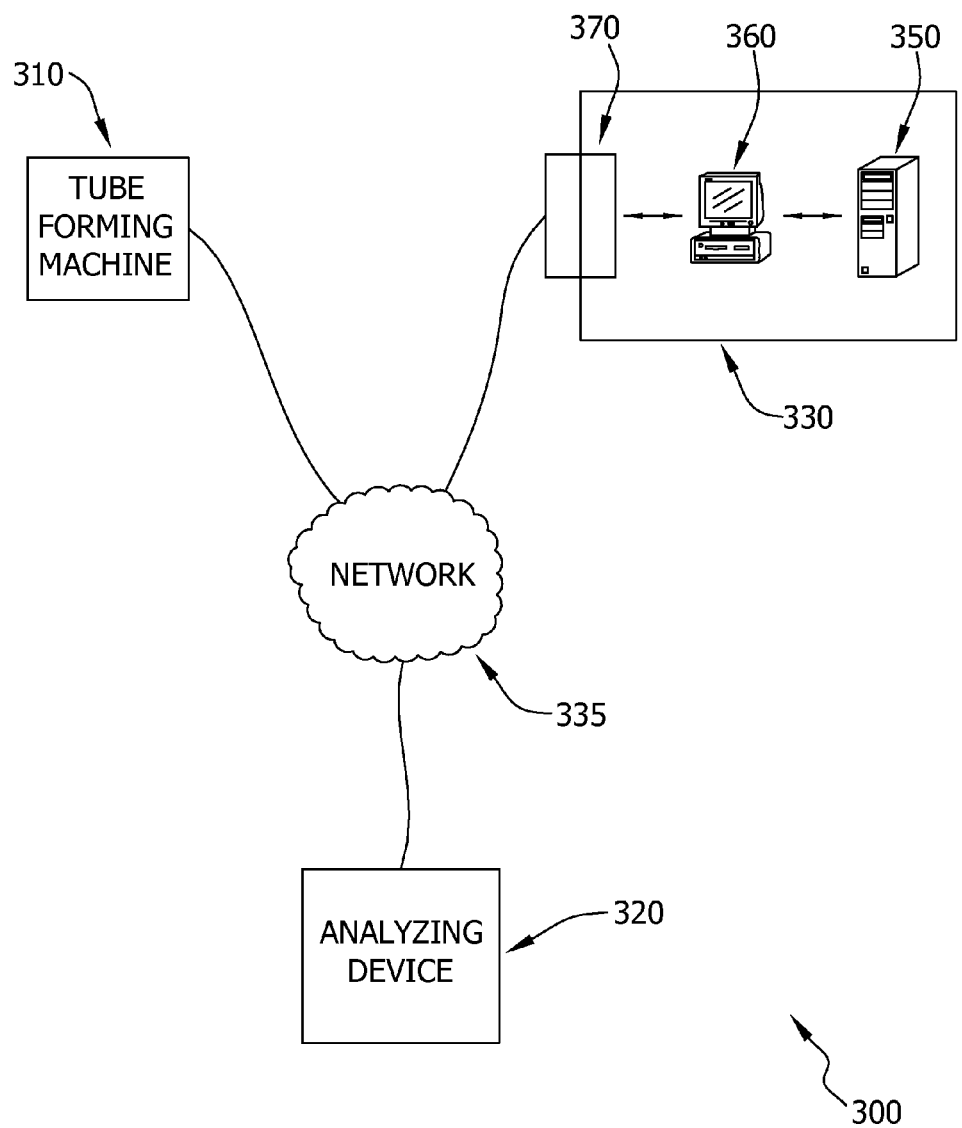
FIG. 4 is a block diagram of one embodiment of a system for manufacturing tubing according to a second embodiment of a method for manufacturing such tubing.

FIG. 4 is a schematic diagram illustrating a system 300 for forming a tube (such as tube 210 of the embodiment of FIG. 1) from a tubing material according to another embodiment of a method for forming such tubing. The method and system 300 of this embodiment includes an extruder and in some instances one or more post-extrusion apparatus (the extruder and post-extrusion apparatus together broadly defining a tube forming machine) 310 for manufacturing tubes, an analyzing device 320 used for determining one or more material properties of a material from which the tubing is to be made, and an operating parameter computing device 330.

In the illustrated embodiment, the tube forming machine 310, the analyzing device 320, and the computing device 330 may be in communication with each other via a network 335. The network 335 may include, without limitation, the Internet, a local area network (LAN), a wide area network (WAN), a wireless LAN (WLAN), a mesh network, and/or a virtual private network (VPN) or other suitable communication means. It is contemplated that one or more of the components may instead be other than in communication via the network 335. For example, it is understood that the computing device 330 may instead be electrically connected directly to and in some instances form part of the extruder. In such an embodiment, the analyzing device 320 may not communicate with the computing device 320 and tube forming machine 310 and remain within the scope of this embodiment. It is also understood the forming machine 310, the analyzing device 320 and/or the computing device 330 may be located remote from each other or two or more of these components may be co-located without departing from the scope of this invention.

The analyzing device 320 is suitably configured for analyzing material to be used for making tubing, and for determining one or more material characteristics of such tubing material. For example, in one embodiment the analyzing device 320 may be capable of determining a durometer, Young's modulus (elastic modulus) or other material characteristics of the tubing material. Additionally, or alternatively, the analyzing device may be capable of determining at least one performance characteristic (e.g., volumetric or dosage delivery accuracy or other performance characteristic) of tubes made from materials having different material characteristics.

It is understood that the analyzing device 320 may comprise a plurality of analytical apparatus, whether co-located or remotely situated. For example, in one embodiment the analytical device 320 may comprise a material analyzer capable of determining one or more material characteristics of tubing material, and a separate test apparatus useful for determining at least one performance characteristic of tubing made from such tubing material.

The operating parameter computing device 330 suitably includes a memory area 350 and a processor 360 coupled to the memory area 350. It should be understood that the computing device 330 may also include input channels and/or output channels. In the embodiments described herein, input channels may include, without limitation, sensors and/or computer peripherals associated with an operator interface, such as a mouse and/or a keyboard. Further, in the exemplary embodiment, output channels may include, without limitation, a control device, an operator interface monitor and/or a display. The memory area 350 may include, without limitation, a computer-readable medium, such as a random access memory (RAM), and a computer-readable non-volatile medium, such as flash memory. Alternatively, a floppy disk, a compact disc-read only memory (CD-ROM), a magneto-optical disk (MOD), and/or a digital versatile disc (DVD) may also be used.

The computing device 330 is configurable to perform various operations described herein by programming the processor 360. For example, the processor 360 may be programmed by encoding an operation as one or more executable instructions and providing the executable instructions to the processor 360 in the memory area 350 coupled to the processor 360.

As used herein, the term "processor" broadly refers to a controller, a microcontroller, a microcomputer, a programmable logic controller (PLC), an integrated circuit, an application specific integrated circuit, and other programmable circuits, and these terms are used interchangeably herein. Additionally, the term "processor" may include multiple processing units (e.g., in a multi-core configuration).

Processors described herein process information transmitted from one or more electrical and electronic devices that may include, without limitation, sensors, actuators, control systems, and/or monitoring devices. Such processors may be physically located in, for example, a control system, a sensor, a monitoring device, a desktop computer, a laptop computer, a PLC cabinet, and/or a distributed control system (DCS) cabinet. RAM and storage devices store and transfer information and instructions to be executed by the processor(s). RAM and storage devices can also be used to store and provide temporary variables, static (i.e., non-changing) information and instructions, or other intermediate information to the processors during execution of instructions by the processor(s). Instructions that are executed may include, without limitation, tube extruding commands. The execution of sequences of instructions is not limited to any specific combination of hardware circuitry and software instructions.

In the exemplary embodiment, the computing device 330 also includes at least one communication interface 370. The communication interface 370 is configured to be coupled in communication with one or more remote devices, such as the tube forming machine 310 and the analyzing device 320. In the illustrated embodiment, for example, the communication interface 370 may be coupled in communication with a remote device via network 335.

The computing device 330 in accordance with one embodiment is suitably configured to receive (and store) data indicative of one or more material characteristics of tubing materials, as well as data indicative of at least one performance characteristic of tubing made from such different tubing materials, and data indicative of tube forming machine 310 operating parameters (e.g., tube dimensions such as inner diameter, wall thickness and length) and to determine a functional relationship (such as in the form of an equation, a look-up table, spreadsheet, etc.) between one or more material characteristics of tubing materials, tube forming machine operating parameters (e.g., tube dimensions) and the corresponding one or more performance characteristics of tubing made from such materials.

In the illustrated embodiment, such data is received, either manually or more suitably via the network 335, as a result of operation of the analyzing device 320. For example, data obtained from the analyzing device 320 may be communicated via the network 335 to the computing device 330, or data output by the analyzing device may be input by a user into the computing device 330.

It is also contemplated that the computing device 330 (e.g., processor 360) is programmed to transform data indicative of one or more material characteristics of a particular tubing material to be used into one or more operating parameters (e.g., tube inner diameter, wall thickness, length, etc.) for operation of the tube forming machine (e.g., the extruder and in some instances post-extrusion apparatus) to produce tubing that results in a predetermined performance characteristic (e.g., delivery accuracy) upon use of the tubing. The computing device, such as via interface 370, communicates such operating parameters to the tube forming machine 310. Alternatively, a user may input such operating parameters into the tube forming machine 310.

Figure 5:
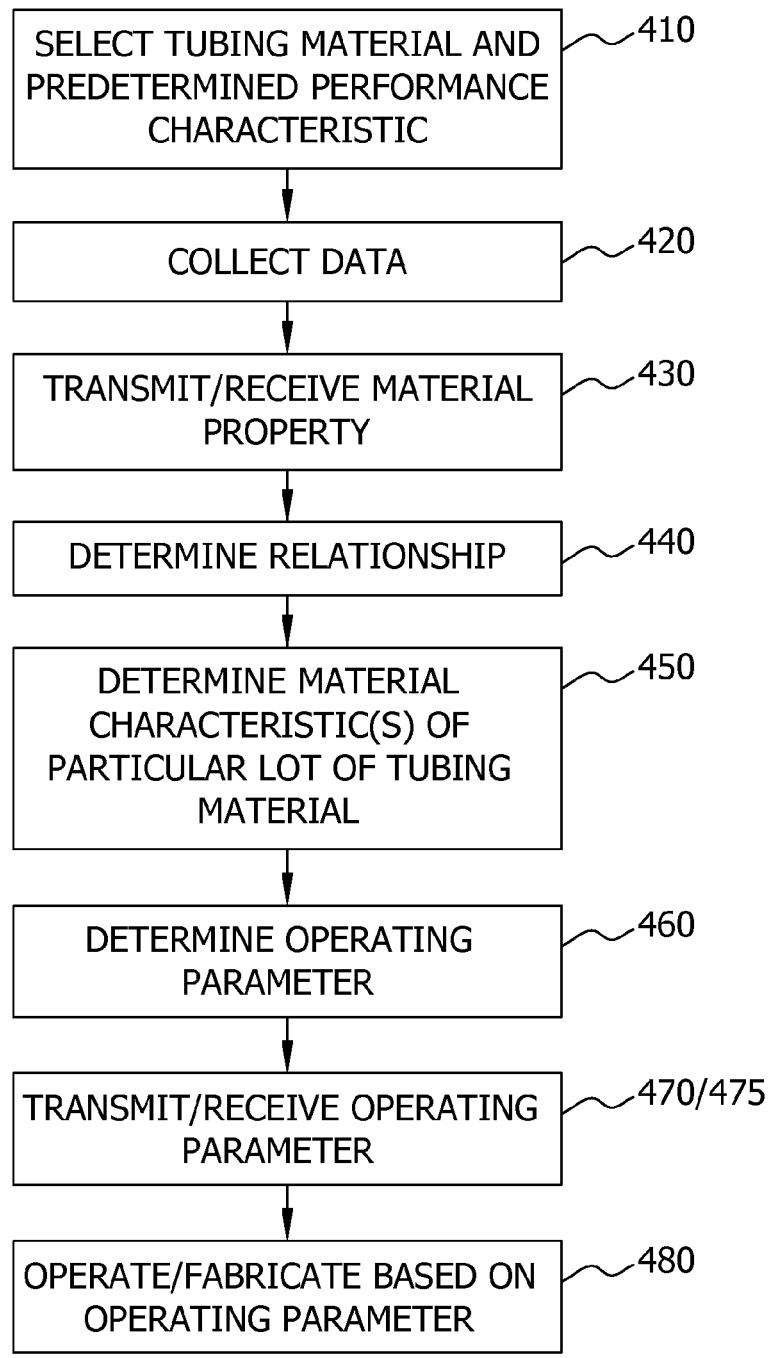
FIG. 5 is a flowchart of an exemplary method for using the system shown in FIG. 3 to form a tube from a tubing material.

FIG. 5 is a flowchart of one exemplary method for extruding the tube 210 from a tubing material using the system 300 of FIG. 4.

At step 410 a particular type of material to be used for fabricating tubes is selected 410, as are theoretical (or nominal) tube forming machine operating parameters such as tube dimensions (e.g., inner diameter, wall thickness, length) of tubes to be used for a particular delivery device to achieve a particular predetermined performance characteristic (e.g., a particular volumetric or dosage delivery). Using the analyzing device 320 (and the tube forming machine 310 to fabricate the tubes), multiple experiments are conducted on tubing materials having different material characteristics (but otherwise the same theoretical or nominal dimensions including inner diameter, wall thickness and length) and the resultant one or more performance characteristics (e.g., delivery accuracy resulting from tubes made from the such tubing materials. This data is collected 420 and delivered 430 to the computing device 320.

The computing device 320 processes the data to determine at 440 a functional relationship (e.g., an equation, a look-up table, etc.) between the material properties of the tubing, the operating parameters of the tube forming machine 310 such as for example the inner diameter, wall thickness and/or length of the tubing, and at least one performance characteristic such as the delivery accuracy.

A manufacturing lot of tubes 210 for use with a particular delivery pump are then ready to be manufactured. In particular, a specific lot of tubing material is analyzed 450 (e.g., by the material supplier, or by the manufacturer such as by using the analyzing device 320 or other suitable device) to determine at least one material characteristic (e.g., durometer, elastic modulus, etc.) of the tubing material and more suitably the deviation of such characteristics from the nominal (e.g., intended) characteristics of such tubing material. These characteristics are input to the computing device 330.

The computing device 330 determines 460 at least one operating parameter of the extruder (e.g., tube inner diameter, wall thickness, length, etc.) based on the relationships determined 440 between the at least one material characteristics, the operating parameter(s) of the tube forming machine 310 (e.g., at least one dimensional characteristic such as inner diameter, wall thickness and length) and the at least one predetermined performance characteristic (e.g., delivery accuracy).

In this manner, the actual material characteristics of the material to be used are transformed into at least one operating parameter (e.g., inner diameter, wall thickness, length, etc.) for operation of the tube forming machine 310 in order to produce tubing that will in use achieve the at least one predetermined performance characteristic (e.g., delivery accuracy). Deviations of the operating parameters of the tube forming machine 310 and in particular of the resultant dimension(s) of the tubing thus account for deviations in the one or more material characteristics of the particular lot of tubing material in order to reduce deviations (e.g., error) in the predetermined performance characteristic such as delivery accuracy.

The computing device 330 and, more specifically, the communication interface 370 transmits 470 the at least one operating parameter to the tube forming machine 310 via the network 335, and the extruder 310 receives 475 the at least one operating parameter from the computing device 330.

The tube forming machine 310 (i.e., the extruder and/or post-extrusion apparatus) is operated 480 based at least in part on the at least one operating parameter (e.g., inner diameter, wall thickness and/or tube length) to form tubes 210 from the tubing material.

When introducing elements of the present invention or the preferred embodiment(s) thereof, the articles "a", "an", "the", and "said" are intended to mean that there are one or more of the elements. The terms "comprising," "including", and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A method for manufacturing tubing to achieve at least one predetermined performance characteristic relating to a flow of a flowable material therethrough, the tubing being formed from a tubing material according to at least one operating parameter of a tube forming machine, said method comprising:

determining a relationship between at least one material characteristic of the tubing material, at least one operating parameter of the tube forming machine, and at least one predetermined performance characteristic of the tubing;

determining, based on said relationship, at least one operating parameter for operation of the tube forming machine to achieve said at least one predetermined performance characteristic;

inputting said at least one operating parameter into the tube forming machine; and operating the tube forming machine to form tubing to achieve said at least one predetermined performance characteristic;

wherein the relationship determining step comprises inputting data indicative of the at least one material characteristic, the at least one operating parameter and the at least one predetermined performance characteristic into a computing device, and operating the computing device to determine from said data a functional relationship between the at least one material characteristic of the tubing material, the at least one operating parameter of the tube forming machine, and the at least one predetermined performance characteristic of the tubing.

2. The method set forth in claim 1 wherein the at least one material characteristic comprises at least one of a durometer and an elastic modulus of the tubing material.

3. The method set forth in claim 1 wherein the at least one operating parameter of the tube forming machine comprises at least one dimensional characteristic of the tubing to be extruded.

4. The method set forth in claim 3 wherein the at least one dimensional characteristic comprises at least one of an inner diameter, a wall thickness and a length of the tubing.

5. The method set forth in claim 1 wherein the relationship determining step comprises determining at least one of a theoretical tube inner diameter, a theoretical tube wall thickness and a theoretical tube length to achieve the at least one predetermined performance characteristic of the tubing, determining a relationship between the at least one material characteristic and at least one of an actual tube inner diameter, an actual tube wall thickness and an actual tube length to achieve the at least one predetermined performance characteristic, said at least one of the actual tube inner diameter, the actual tube wall thickness and the actual tube length being different from the respective at least one of the theoretical tube inner diameter, the theoretical tube wall thickness and the theoretical tube length.

6. The method set forth in claim 5 wherein the operating parameter determining step comprises determining, based on said relationship and the material from which tubing is to be formed, at least one operating parameter for operation of the tube forming machine to form tubing having said at least one of the actual tube inner diameter, the actual tube wall thickness and the actual tube length.

7. The method set forth in claim 1 wherein the operating parameter determining step comprises inputting to a computing device the determined relationship, inputting to said computing device at least one material characteristic of a particular lot of tubing material from which tubes are to be extruded, and operating the computing device to determine said at least one operating parameter.

8. The method set forth in claim 1 wherein the tube forming machine comprises an extruder.

9. The method set forth in claim 8 wherein the tube forming machine further comprises cutting apparatus for cutting tubing formed by the extruder to a predetermined length of tube.

10. The method set forth in claim 9 wherein the cutting apparatus is located remote from the extruder.

\* \* \* \* \*